United States Patent [19]

Pierce

[11] Patent Number: 4,823,794
[45] Date of Patent: Apr. 25, 1989

[54] SURGICAL PLEDGET

[76] Inventor: William S. Pierce, 1201 Saradana Rd., Harrisburg, Pa. 17112

[21] Appl. No.: 676,601

[22] Filed: Dec. 3, 1984

Related U.S. Application Data

[63] Continuation of Ser. No. 397,484, Jul. 12, 1982, abandoned.

[51] Int. Cl.⁴ .............................................. A61B 17/00
[52] U.S. Cl. ...................................................... 128/335
[58] Field of Search ............... 128/334 R, 334 C, 335, 128/335.5, DIG. 26; 24/128 R, 17 AP

[56] References Cited

U.S. PATENT DOCUMENTS

| | | | |
|---|---|---|---|
| 815,264 | 3/1906 | Chambers | 128/334 R |
| 1,635,066 | 7/1927 | Wells | 128/334 R |
| 2,952,206 | 9/1960 | Becksted | 24/129 R |
| 3,254,651 | 6/1966 | Collito | |
| 3,357,432 | 12/1967 | Sparks | |
| 3,541,591 | 11/1970 | Hoegerman | 128/335 |
| 3,696,920 | 10/1972 | Lahay | 128/DIG. 26 |
| 3,753,438 | 8/1973 | Wood et al. | |
| 3,789,851 | 2/1974 | LeVeen | |
| 3,831,608 | 8/1974 | Kletschka et al. | 128/335 |
| 3,885,570 | 5/1975 | Leveen | 128/335 |
| 4,063,638 | 12/1977 | Marwood | 128/335.5 |
| 4,217,665 | 8/1980 | Bex et al. | |
| 4,291,698 | 9/1981 | Fuchs et al. | 128/335 |

FOREIGN PATENT DOCUMENTS 215065  5/1961  Austria ................. 128/335

OTHER PUBLICATIONS

'A Tech. for Rapid One Layer Abdominal Closure', Surg., Gyne. & Obstet., vol. 124, 2/1967, Broaddus, pp. 359–361.
Ethicon Advertisement, showing Pledgets.
Reed and Cortes, Measured Tricuspid Annuloplasty: A Rapid and Reproducible Technique, Annuals of Thoracic Surgery, vol. 21, Feb. 1976, pp. 168–169.
American Cyanamid Company, Pearl River, NY, attached specimens of Polymer Pledgets.

*Primary Examiner*—Richard J. Apley
*Assistant Examiner*—Paul Prebilic
*Attorney, Agent, or Firm*—Thomas Hooker

[57] ABSTRACT

A surgical pledget including a suture entrance slit extending through the pledget from a side wall to a central suture location within the pledget and means for retaining the suture at the suture location so that the pledget may be positioned on a medial portion of a suture.

12 Claims, 1 Drawing Sheet

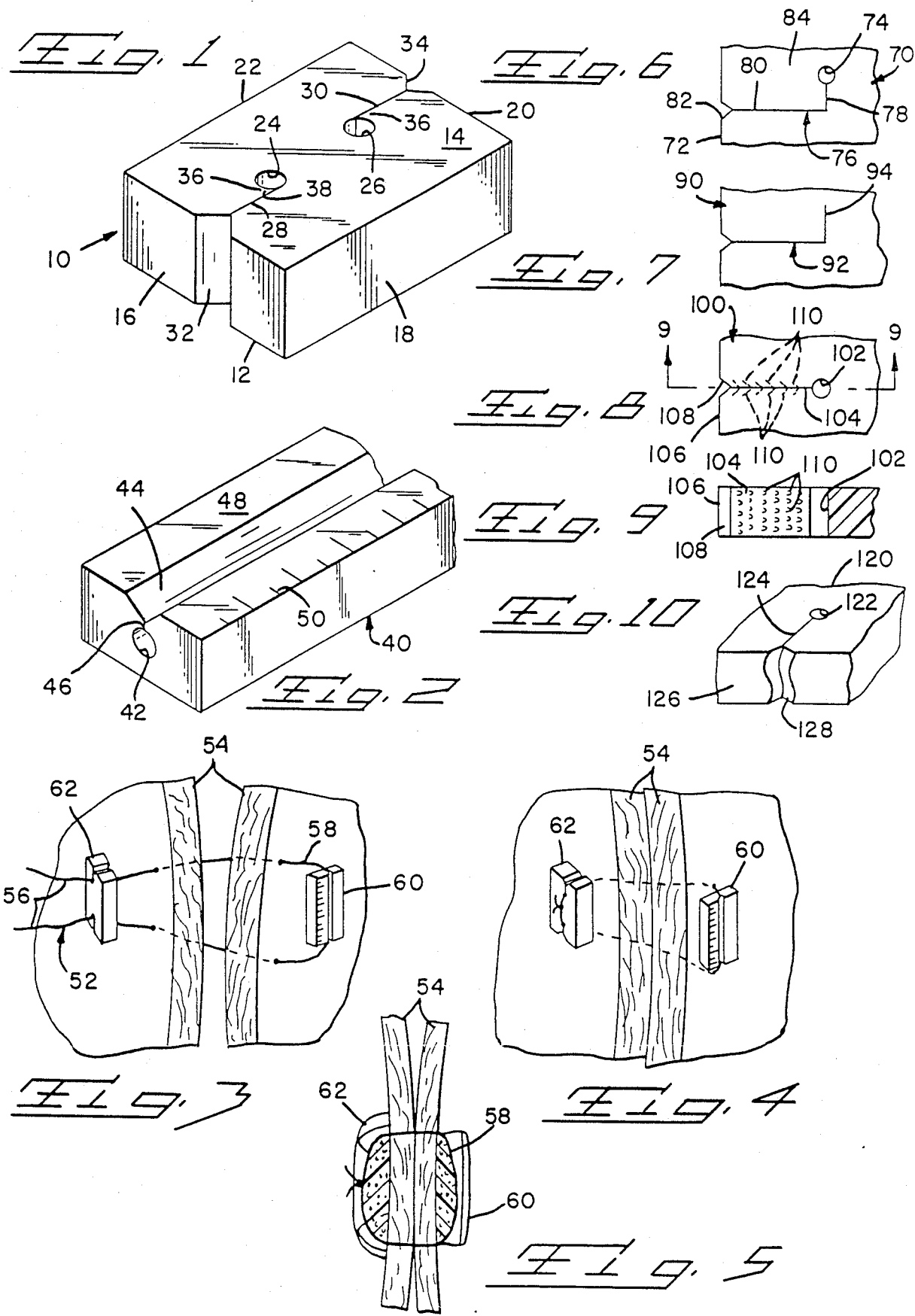

SURGICAL PLEDGET

This application is a continuation of Pierce U.S. Ser. No. 397,484 for "Surgical Pledget", filed July 12, 1982, now abandoned.

The invention relates to an improved surgical pledget which may be attached to a medial portion of a suture strand before or after the strand has been passed through tissue.

Pledgets are small pieces of thin resilient material employed in cardiovascular surgery to distribute the tension of a suture over a broad area. They are conventionally formed from a resilient material such as polyurethane foam, felt or a Teflon fabric and have sufficient flexibility to assure that after the suture strand is tied the pledget is held against the tissue surrounding the suture to prevent tearing of the strand through the tissue and to reduce or prevent bleeding at suture puncture wounds. Pledgets are conventionally formed from flat sheet stock material and may be circular or rectangular in shape.

Pledgets are currently supplied in loose pieces with or without preformed suture holes extending through the pledget thickness. When these types of pledgets are used, suturing includes the step of threading the strand through the pledgets. In the case the suture is double-armed with needles at both ends, the suture nurse prepositions a bight pledget on the strand prior to handing the suture to the surgeon. The surgeon then passes the needles through the tissue and, as an extra step, passes the needles through another pledget on the knot-side of the suture. The suture is then drawn tight, the ends of the suture are tied together and the needles and excess strand material are snipped away to complete the suturing operation.

In the event the suture is single-armed having a needle on one end only, the suture nurse must first pass the needle through the pledget on the knot side of the suture following which the surgeon must pass the needle through the tissue to be joined, pass the needle twice through the bight pledget, pass the needle back through the tissue and through the knot pledget prior to drawing the suture tight and completing the suture by knotting the ends of the strand on the outside of the knot pledget.

Mattress suturing using pledgets is described in Reed and Cortez, "Measured Tricuspid Annulopasty: A Rapid and Reproducible Technique", *Annals Of Thoracic Surgery*, Vol. 21, February, 1976, pp. 168–169. Conventional pledgets are available from a number of sources. Double-armed sutures with pre-threaded bight pledgets are marketed by Ethicon, Inc. of Sommerville, N.J. Loose piece pledgets with pre-punched suture holes are available from American Cyanamid Company of Pearl River, N.Y.

The use of current pledgets requires complex surgical operations increasing surgery time and, as a result, increases the chance for surgical error. A surgeon may decide not to use pledgets and thereby sacrifice their advantages for the patient. For instance, surgeons frequently do not use pledgets on purse-string sutures because of necessity to pass the suture needle through pledgets after each tissue bite.

Additionally, with conventional pledgets, it is difficult or impossible for the surgeon to affix a pledget on a partially formed suture in the event he determines it is desirable to use a pledget after the suture has been initially passed through the tissue. When a single armed-suture is used, a knot pledget cannot be placed on the suture after the first tissue bite.

The disclosed pledgets are formed from conventional pledget material and include a normally closed suture entrance slit extending from one side of the pledget to a central strand location extending through the pledget away from the side of the pledget, thereby allowing the surgeon to affix the pledget to a medial part of the strand. The pledget is simply and easily affixed to the suture by first aligning the pledget slit adjacent the strand and then moving the strand along the slit to the central location. The slit allows the strand to be easily moved into the pledget but resists removal of the strand from the pledget so that the pledget is held in place on the strand during passage of the strand through tissue, tensioning of the strand and final tying. The suture may be positioned in the central location at the bottom of the slit or, in the case of relatively large diameter suture strands which cannot be accommodated by the resiliency of the pledget material, a preformed suture hole is provided at the bottom of the slit.

One pledget according to the invention includes a flat pledget body with a pair of spaced entrance slits extending into the interior of the body from opposite sides so that the suture strand may be passed through each slit and moved to the central locations. In this pledget the central locations extend across the thickness of the pledget body. In another pledget, a single slit extends across the width of the pledget and the strand is moved through the slit to the central location in a single operation. This type of pledget is easily mounted on the suture in a single operation. The single slit pledget is particularly adapted for attachment to the bight portion of partially completed sutures. It may be cut from an indefinite length of uniform cross section pledget stock so that the surgeon can have the suture nurse provide a pledget of exactly the correct length required for a particular suture required during surgery.

Other objects and features of the invention will become apparent as the description proceeds, especially when taken in conjunction with the accompanying drawings illustrating the invention, of which there is one sheet and six embodiments.

IN THE DRAWINGS

FIG. 1 is a perspective view of a two-slit pledget according to the invention;

FIG. 2 is a perspective view, partially broken away, of an indefinite length of pledget material which may be cut into single slit pledgets of desired length;

FIGS. 3, 4 and 5 illustrate the formation of mattress sutures using one single-slit pledget and one two-slit pledget;

FIGS. 6, 7, and 8 are top views, partially broken away, of different types of pledgets similar to the pledget of FIG. 1;

FIG. 9 is a sectional view taken along line 9—9 of FIG. 8; and

FIG. 10 is a side view of a still further pledget similar to the pledget of FIG. 1.

Pledget 10 as shown in FIG. 1 includes a body 12 formed from a conventional pledget material such as felt, polyurethane foam or a Teflon having sufficient resiliency so that the pledget is compressed somewhat by the suture and is held tightly against the tissue being sutured. The body 12 is preferably cut from relatively thin pledget sheet strip stock and includes a major surface 14, an opposite major surface (not illustrated) parallel to surface 14 and side walls 16, 18, 20 and 22 extending across the thickness of the pledget and joining the major surfaces. Suture holes 24 and 26 are formed through the thickness of the pledget 10 at central suture locations adjacent walls 16 and 20 respectively. The holes are connected to their respective adjacent side walls by normally closed entrance slits 28 and 30. V-shaped lead-ins 32 and 34 are provided at the ends of the slits adjacent the side walls. The slits and lead-ins extend through the thickness of the pledget between the major surfaces to facilitate movement of a medial portion of the suture strand to the central locations.

As shown in FIG. 1, slits 28 and 30 intersect holes 24 and 26 tangentially thereby permitting the medial portions of the strand to be moved easily through the slits and into the holes while preventing ready removal of the medial portions from the holes. The holes have approximately the same diameter as the strand, so that the suture extends freely through the holes and may be easily drawn through the pledget.

The tangential intersection between the slit and the hole provides a slit-free pledget portion 36 on the side of the pledget hole adjacent the nearest side wall. This portion resists movement of the strand outwardly of the hole toward the adjacent side wall. The intersection between the slit and the hole is located away from the wall, with the slit extending tangentially from the hole so that forces tending to move the suture radially outwardly of the hole bring the suture into contact with the pledget material without finding the slit. The continuous portion includes a tip 38 at the end of the slit which extends away from the wall. When the suture in the hole is moved toward the adjacent side wall the tip guides the suture strand away from the slit and into contact with the portion which resists withdrawal.

FIG. 2 illustrates an indefinite length of pledget stock material 40 having a single continuous suture hole 42 extending longitudinally along the length of the material with a lead-in 44 and slit 46 connecting the hole to one of the adjacent major surfaces 48.

Individual pledgets are cut from the stock material 40 so that the pledget hole 42 extends between opposite sides of the pledget. The stock material is formed with length-indicating scale 50 extending longitudinally along one surface to facilitate cutting individual pledgets to a length appropriate for the particular suture application.

The medial portion of a suture strand may be easily moved into a pledget hole 42 of a pledget cut from stock material 40 by piloting the suture into the lead-in 44 and thence through the slit 46 and into the hole in a single step. The resilient pledget material deforms during passing of the strand through the slit and then snaps back to close the slit after the strand is in the hole. If desired, the lead-in and slit may be positioned laterally of the hole so that the slit is tangential with the hole, thereby facilitating improved retention of the suture within the hole, as previously described. The suture hole 42 preferably is about the same diameter as the strand used with the pledget.

FIG. 3 illustrates use of pledgets of the FIG. 1 and FIG. 2 types for closing a surgical incision using a mattress-type suture. Suture 52, whether single-armed or double-armed is passed twice through tissue segments 54 so that both suture ends 56 are on one side of the tissue segments and a suture bight 58 is formed on the opposite side of the tissue. A bight pledget 60 of the type formed from the pledget stock material 40 of FIG. 2 is attached to the strand 58 by piloting part of the bight into the lead-in 44 and then moving the portion past the slit 46 and into the pledget hole 42.

A pledget 62 similar to pledget 10 of FIG. 1 is attached to the knot end of the suture away from the bight 58. The ends of the suture strand are piloted into a lead-ins 32 and 34 and then are forced through slits 28, 30 and moved into the suture holes 24, 26 so that the pledget is firmly mounted on the suture. The pledget is momentarily deformed as the strands are moved to the holes and then resumes its original shape. The suture is then drawn tight to close the spacing between the tissue segments 54 and draw resilient pledgets 60 and 62 flush against the tissue. The surgeon ties the suture ends 56 together on the major surface of pledget 62 to complete the mattress suture shown in FIG. 4. Before tying the knot, the suture is drawn sufficiently tight to compress the pledgets against adjacent tissue surfaces thereby assuring that upon completion of the knot and snipping off of the free suture ends 56, as illustrated, the inherent resiliency of the pledget material maintains the suture taut with the major pledget surfaces held snugly against the adjacent tissue surfaces.

The taut suture holds the tissue segments 54 together thereby retaining the tissue segments closed as shown in FIG. 4. The pledgets 60 and 62 distribute the tension over a relatively large tissue surface, thereby reducing possible tearing of the tissue at the suture. Additionally, the resilient pledget material is forced into close contact with the tissue at the suture puncture sites to reduce or prevent bleeding.

FIGS. 4 and 5 illustrate a conventional mattress-type suture using different forms of pledgets according to the invention as previously described. In practice, it may be more convenient to use similar pledgets of either type for forming a mattress suture, depending upon the particular surgical procedure involved. For instance, it may be desirable to use a pledget of the type shown in FIG. 1 where there is particular concern about preventing bleeding at the suture site. This type of pledget extends completely around the suture puncture wound and is drawn against the surrounding tissue. In contrast, pledgets of the type formed from pledget material shown in FIG. 2 may be preferred in certain surgical procedures where there are advantages in using pledgets of a desired length and ease of mounting on the suture is a concern.

FIGS. 6 through 10 illustrate additional pledgets similar to the pledget of FIG. 1 with different suture entrance slits and central suture locations. FIG. 6 is a partial top view of a pledget 70 having a side wall 72 and a suture hole 74 extending between the major surface top and bottom. An L-shaped suture entrance slit 76 extends between the hole and side wall and includes a first leg 78 extending from hole 74 a short distance parallel to side wall 72 and a second major leg 80 extending from leg 78 in a direction toward the side wall 72 to V-shaped lead-in 82. The pledget 70 may be similar to pledget 10 and include a pair of suture holes 74 each having an L-shaped entrance slit extending to an adjacent pledget side wall.

A suture strand is moved to the suture hole 74 by piloting a medial portion of the strand into the lead-in and then moving the strand through the L-shaped slit so that it is fitted within the hole. The pledget includes a continuous slit-free portion 84 on the side of the hole adjacent the side wall 72 to aid in retention of the strand in the hole. Forces tending to move the strand directly toward the side wall 72 contact the continuous pledget portion 84 to resist separation of the suture from the pledget.

Pledget 90 shown in FIG. 7 is identical to pledget 70 of FIG. 6 except that the pledget is not provided with a specially formed suture retention hole at the central suture location 94 located at the inner end of the L-shaped entrance slit 92. This type of surgical pledget is used with small diameter suture strands where the pledget material has sufficient resiliency to receive and retain the suture strand at the end of the slit without a preformed hole. For instance, pledget 90 may be used when forming sutures with suture strands having a diameter approximately equal to the diameter of a human hair. Larger diameter strands may be held in pledgets of this type without suture holes provide that the pledget material has sufficient resiliency to surround the strand at the end of the entrance slit without undue deformation of the pledget while allowing the strand to be readily drawn through the pledget during suturing. Thus, it is contemplated that for some applications, the pledgets as disclosed may not require preformed pledget holes such as holes 24, 26, 42 and 74 at the central suture locations.

FIGS. 8 and 9 illustrate a pledget 100 having a suture hole 102 extending between the major faces, a suture entrance slit 104 extending from the suture hole toward adjacent side wall 106 and joining the side wall at V-shaped lead-in 108. The side walls of slit 104 are provided with strand retention elements 110 which extend from the side walls in a direction toward the suture hole as illustrated in FIG. 8 and serve to resist withdrawal of the suture strand from the pledget. The retention members may be bristles formed of the pledget material. A portion of the strand is moved into the suture hole 102 through the slit 104. Once seated within the hole, retrograde movement outwardly of the hole along the slit is resisted by the retention members, even though the slit extends directly from the hole 102 to the side wall 106.

FIG. 10 illustrates one side wall and part of the top wall of a pledget 120 having a pledget hole 122 and a suture entrance slit 124 extending from the hole to adjacent side wall 126. A V-shaped lead-in 128 joins the end of the slit and the side wall.

In contrast to the straight entrance slit of the previously described pledgets, slit 124 is curved from top to bottom so that a strand moved through the slit to the suture hole 122 is bent and then is straightened as it fits within the straight suture hole. The curved slit resists removal of the strand from the pledget.

The pledgets of FIGS. 6 through 10 have been described as having a pair of spaced pledget holes or central suture locations so that the suture strand extends through one hole or location, across a central portion of a major pledget surface and back through the other hole or location. It is contemplated that suture entrance slits of the types shown in FIGS. 6 through 10 may be used in pledgets with a single entrance slit and hole or centered suture location. In these cases the tied strand extends across the width of the pledget as in pledget 60 formed from the pledget stock material illustrated in FIG. 2.

The V-shaped suture lead-ins aid the surgeon in properly positioning the strand at the mouth of the slit and guide the strand as it moves into the resilient pledget so that it finds the slit. In some situations it may be desirable to color code the lead-ins to further facilitate rapid positioning of the suture for movement into the slit.

As illustrated, entrance slits 28, 30, 46, 76, 92, 104 and 124 are formed in their respective pledget bodies and are normally closed. The slits each include a pair of slit side walls extending through the resilient pledget material and abutting each other to normally close the slit and resist movement of a suture strand through the slit. Forceable movement of a suture strand to the end of a slit momentarily opens the slit by compressing the pledget material. The slit closes after the strand has been properly seated as described.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim my invention is:

1. A pledget for use in cardiovascular surgery to distribute the tension of a suture strand over a broad area of cardiovascular tissue, the pledget including an integral body consisting of a single piece of soft, resilient and suture compressable pledget material, the body including a surface adapted to engage cardiovascular tissue to be sutured, a wall, a suture strand hole extending through the body away from the wall permitting a suture strand to be freely drawn through the hole during suturing, and a slit extending from the wall to the hole, the slit intersecting the hole tangentially, the resiliency of the pledget material keeping the slit closed with opposed sides of the slit abutting each other except while an acute angle suture strand is passed through the slit to the hole, the body including a continuous portion on one side of the hole with the portion including an acute angle tip at the junction of the slit and the hole whereby upon movement of of a suture strand from the wall, along the slit, past the portion and into the hole the portion engages the strand and resists withdrawal of the strand from the hole along the slit.

2. A pledget as in claim 1 wherein said slit is nonplanar.

3. A pledget as in claim 2 wherein said slit includes two generally planar legs.

4. A pledget as in claim 3 wherein said slit is L-shaped.

5. A pledget as in claim 2 wherein said slit is curved.

6. A pledget as in claim 1 includes means in the slit resisting withdrawal of a suture strand from the hole.

7. A pledget for use in cardiovascular surgery to distribute the tension of a suture strand over a broad area of cardiovascular tissue, the pledget including an integral body consisting of a single piece of soft, resilient and suture compressable pledget material, the body including a surface adapted to engage cardiovascular tissue to be sutured, a wall, a suture strand location extending through the body away from the wall, and a non-planar slit extending through the thickness of the body from the wall to the suture strand location, the resiliency of the body keeping the slit closed with opposed sides abutting each other except when a suture strand is moved through the slit to the suture strand location whereby a suture strand may be moved from the wall through the slit to the suture strand location, the closed non-planar slit resisting withdrawal of the suture strand from the suture strand location.

8. A pledget as in claim 1 wherein the suture location comprises a hole extending through the body.

9. A pledget as in claim 8 wherein the slit intersects the hole tangentially.

10. A pledget as in claim 7 wherein the slit includes two generally planear legs.

11. A pledget as in claim 10 wherein said slit is L-shaped.

12. A pledget as in claim 7 wherein the slit is curved.

* * * * *